United States Patent [19]

Gernez

[11] Patent Number: 5,137,690

[45] Date of Patent: Aug. 11, 1992

[54] PROCESS AND APPARATUS FOR THE DETERMINATION OF THE IODINE CONTENT OF DRINKING WATER

[75] Inventor: Gérard Gernez, Villemoisson sur Orge, France

[73] Assignee: Rhone-Poulenc Sante, Antony, France

[21] Appl. No.: 603,486

[22] Filed: Oct. 26, 1990

[30] Foreign Application Priority Data

Oct. 27, 1989 [FR] France ................................ 89 14130

[51] Int. Cl.⁵ .................... G01N 21/01; G01N 33/20; G01N 31/22
[52] U.S. Cl. ........................................ 422/57; 422/59; 422/61; 422/82.05; 422/102; 436/125; 436/810
[58] Field of Search ............... 436/124, 125, 182, 808, 436/810; 422/61, 82.05, 82.09, 99, 102, 57, 59, 100; 206/222

[56] References Cited

U.S. PATENT DOCUMENTS

| | | | |
|---|---|---|---|
| 3,615,222 | 10/1971 | Mead | 23/230 |
| 3,705,012 | 12/1972 | Marmor et al. | 23/253 R |
| 3,932,222 | 1/1976 | Dorn | 195/127 |
| 4,125,376 | 11/1978 | Razulis | 23/230 R |
| 4,639,419 | 1/1987 | Olson | 435/5 |
| 4,731,332 | 3/1988 | Blumenthal | 436/61 |
| 4,786,604 | 11/1988 | Michael | 436/77 |
| 5,071,769 | 12/1991 | Kundu | 436/128 |

FOREIGN PATENT DOCUMENTS 3246132  6/1984  Fed. Rep. of Germany .

OTHER PUBLICATIONS

Corning Laboratory Products, Pyrex Labware, Corning Glass Works, Corning, New York, 1971, p. 235.
Flaschka, H. A. et al. "Quantitative Analytical Chemistry" 2nd ed., Willard Grant Press, Boston, Mass. 1980, 451-452.
Lauber, K. "Iodine Determination in Biological Materials of the Catalytic Activity of Iodine" Analytical Chem. vol. 47, No. 4, pp. 769-771, 1975.
Lambert, J. L. et al. "Iodine Determination in the Parts-per-Billion Range with Leuco Crystals Violet and N-Chlorosuccinimide-Succinimide Reagents", Analytical Chemistry vol. 47, No. 6, pp. 915-916, May 1975.
French Search Report dated Jun. 12, 1990.
"Determination of Total Iodine and Iodate-Iodine in Natural Freshwater", Analyst, vol. 107, No. 10, Dec. 1982, pp. 1117-1121, S. D. Jones et al.
Standard Test Methods for Iodide and Bromide in Water, 1987 Annual Book of ASTM Standards, vol. 1101, D1246-82a, pp. 522-530.

*Primary Examiner*—James C. Housel
*Assistant Examiner*—David Redding
*Attorney, Agent, or Firm*—Morgan & Finnegan

[57] ABSTRACT

A process and apparatus for the determination of the iodine content of drinking water by comparing the coloration of the water to be analyzed with that of an iodine reference solution in the presence of a fixed amount of cerium and arsenic.

6 Claims, 2 Drawing Sheets

PROCESS AND APPARATUS FOR THE DETERMINATION OF THE IODINE CONTENT OF DRINKING WATER

FIELD OF THE INVENTION

The present invention relates to a process for the determination of the iodine content of drinking water.

BACKGROUND OF THE INVENTION

In humans, the lack or deficiency in iodine leads to particularly important pathological disorders whose principal ones are, on the one hand, goiter and its complications (deglutition disorders, respiratory disorders, cancer formation, collateral circulation) and, on the other hand, hypothyroidism and its complications (cretinism, cerebral disorders, premature deliveries, miscarriages, congenital anomalies).

Even if iodine deficiency has disappeared in the industrialized countries, this is not the case in developing countries (Latin American countries along the cordillera of the Andes, and the non-coastal countries of Africa and Asia).

Of the different methods proposed for remedying this deficiency, the most effective one consists in adding iodine to the water for domestic use (drinking, washing, irrigation) which most frequently is made available by wells and drillings.

Many studies have shown that a daily supply of about 100 μg of iodine equivalent per day and per person would be sufficient for preventing the development of endemic goiter.

Because it is known that an individual takes up on average 2 liters of water per day, it is desirable that one liter of treated water should contain at least 50 μg per liter of iodine.

There are various systems which make the controlled release of iodine into well or drilling water possible, and it is of particular importance to be able to control the effective iodine content in water.

DETAILED DESCRIPTION OF THE INVENTION

According to the present invention, a method has been found which enables people who have no particular scientific knowledge to evaluate on site in a few minutes, with a minimum of handling and in complete safety whether the iodine content of drinking water is greater than or equal to 50 μg per liter.

According to the invention, the method consists in comparing the coloration of the water to be analyzed to that of an iodine reference solution in the presence of a fixed amount of cerium and arsenic.

The process according to the invention is based on a colorimetric method originating from the implementation of the Sandell-Kolthoff reaction, the steps of which are as follows:

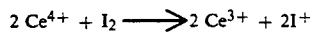

Because it is known that the $Ce^{++}$ ion is yellow in solution and the $Ce^{3+}$ ion is colorless, the presence of iodine in the medium will lead to less coloration of the initial solution containing the $Ce^{++}$ ions. Thus, by comparing the coloration of the water to be analyzed in the presence of cerium and arsenic to that of the reference solutions, the iodine content of the analyzed water can be determined after a certain period of time.

Figure 1:
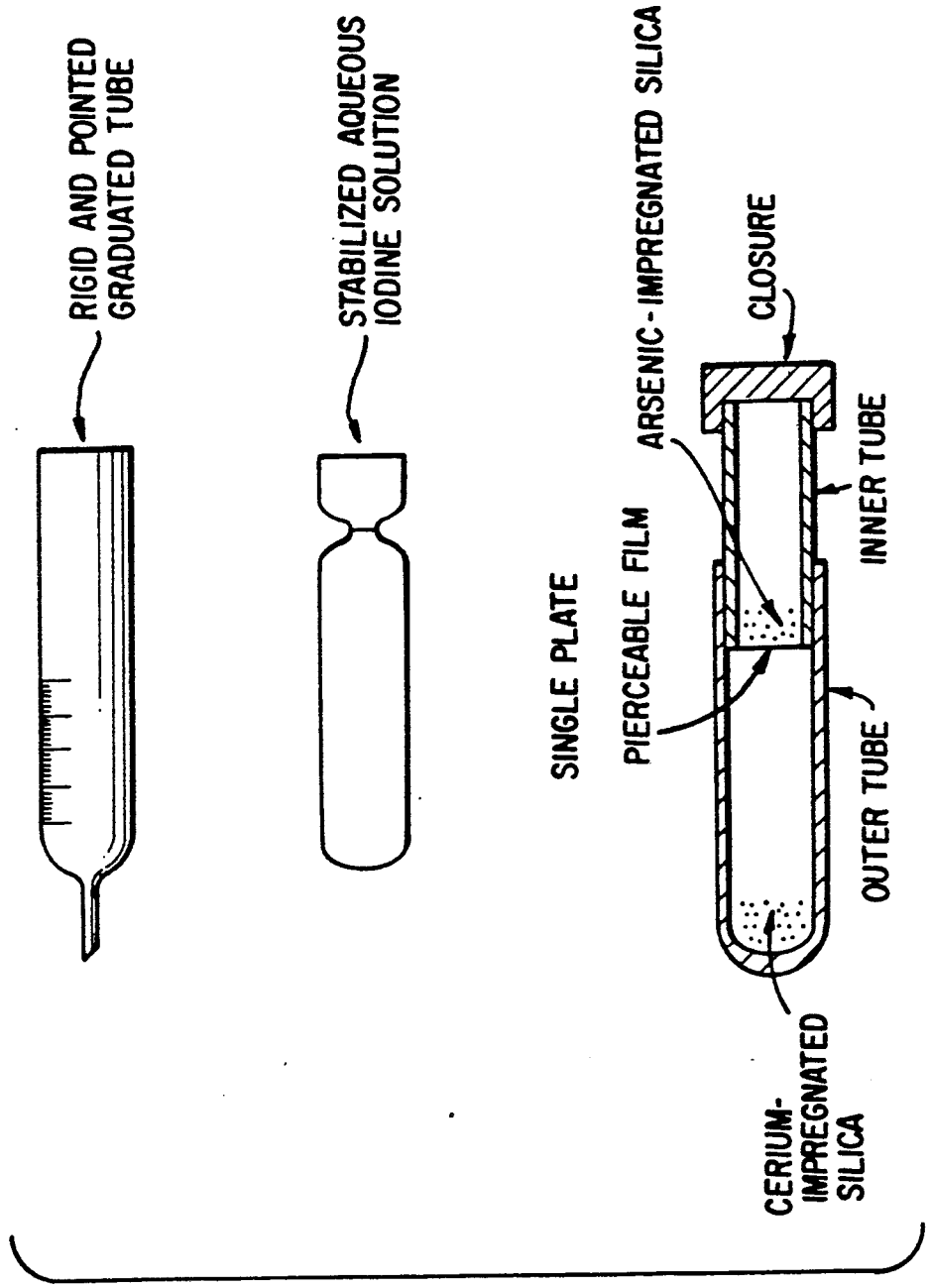
FIG. 1 is a drawing showing the assay kit consisting of the transparent colorless coaxial tubes, the rigid and pointed graduated tube, and the closed tube.
Figure 2:
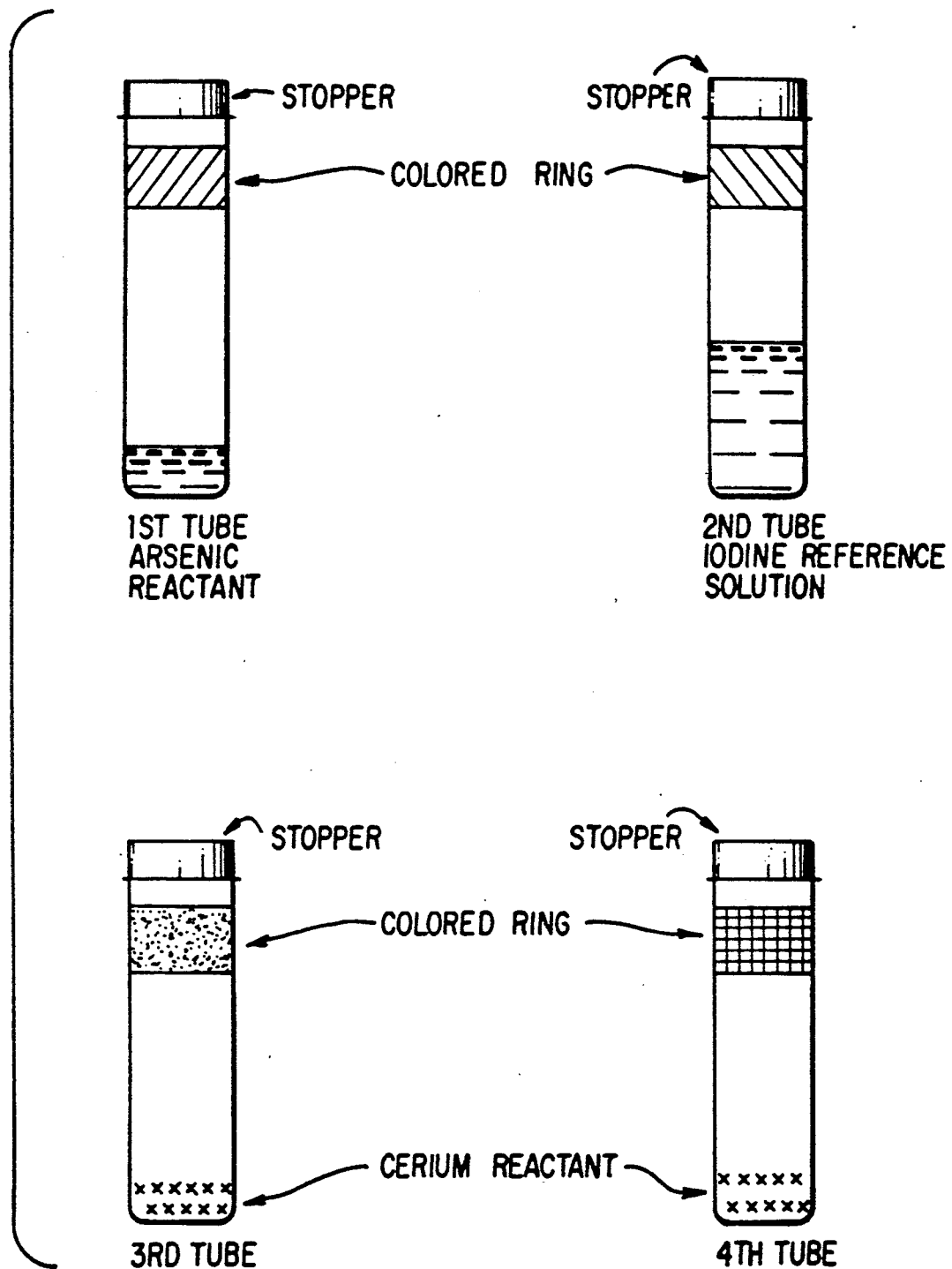
FIG. 2 is a drawing showing the alternative embodiment consisting of the assay kit using four tubes.

The process according to the invention can be carried out by an apparatus consisting of two transparent, colorless coaxial tubes:

an outer tube closed at one end contains a support (silica) containing a fixed amount of a cerium derivative (cerium ammonium sulphate hydrate), an inner tube whose outer diameter corresponds to the inner diameter of the outer tube and which is partially engaged in the outer tube. The inner tube is closed at its end located in the inside of the outer tube by means of a pierceable film and contains a support (silica) containing a fixed amount of an arsenic derivative (arsenic oxide). The outer portion of the inner tube is closed by means of a removable closing system. The apparatus is shown in FIG. 1.

In general, the outer tube has a diameter close to 1 cm, and the thickness of the wall is close to 1 mm. The length of the outer tube between its closed end and the pierceable film is close to 6 cm.

The outer and inner tubes can be made of glass or of a transparent, rigid and colorless plastic material (polystyrene). It is imperative that the material of which the tubes are made be insensitive to reactants and to iodine.

The apparatus described above functions in the following manner:

The removable closure is taken off the inner tube, a fixed amount of water (1 cc) is introduced for testing by means of a rigid and pointed tube, the film is pierced, the removable closure is replaced and the apparatus is carefully shaken. After letting stand for several minutes, the coloration of the solution obtained is compared to that of the reference solutions.

The support containing the cerium derivative can be prepared as follows:

a) Analytically pure cerium ammonium sulphate dihydrate (2.50 g) and 0.5M sulphuric acid (56 cc) are introduced into a 100 cc volumetric flask and made up to 100 cc with twice-deionized water.

b) Silica (TIXOSIL 38 A) (5 g), the solution prepared above (25 cc) and 0.5M sulphuric acid (51 cc) are introduced into the flask of a rotary evaporator. The mixture is evaporated to dryness at 60° C. under reduced pressure (17 mm Hg; 2.26 kPa). The weight of the residue must be slightly less than 13 g. It is made up to 13 g by adding twice-deionized water, the powder obtained is then homogenized and placed at the bottom of the outer tube.

The support containing the arsenic derivative can be prepared in the following manner:

a) Analytically pure arsenic oxide (0.5 g) and analytically pure sodium chloride (0.8 g) are introduced into a 100 cc volumetric flask. 10 cc of 1M sodium hydroxide solution are added, and the mixture is made up to 100 cc.

b) Silica (TIXOSIL 38 A) (5 g) and the solution prepared above (25 cc) are introduced into the flask of a rotary evaporator. The mixture is evaporated to dryness at 60° C. under reduced pressure (17 mm Hg; 2.26 kPa). The weight of the residue obtained is close to 12 g. The powder obtained is homogenized and placed in the inner tube.

In general, when it is desired to determine iodine concentrations close to 50µg per liter, the outer tube contains 100 mg of powder containing the cerium derivative and the inner tube contains 100 mg of powder containing the arsenic derivative.

The process according to the invention can also be carried out by a system consisting of 4 tubes made of glass or of a transparent, rigid and colorless plastic material (polystyrene), each of which is identified by a different colored ring and stopper in order to identify and distinguish between the tubes, and a 2 cc sampling tube.

The tubes contain the following reactants, respectively:

first tube: an amount of the arsenic reactant (0.1 cc), the preparation of which is described below second tube: an iodine reference solution (2 cc), the preparation of which is described below third and fourth tubes: a silica support (200 mg) containing the cerium, the preparation of which has been described above.

The system functions as follows:

Water (2 cc) for testing is sampled by a sampling tube and placed in the tube containing the arsenic reactant. The tube is closed and carefully shaken by turning it over several times in succession.

The contents of the first and second tubes are then transferred to the third and fourth tubes, respectively. The tubes are then stoppered and carefully shaken by turning them over several times in succession. The suspensions obtained are yellow. They are allowed to stand, and the discoloration of the suspensions present in the third and fourth tubes are then noted. If the suspension of the third tube (test) is discolored more rapidly than that of the fourth tube (reference), the water to be analyzed contains more than 50 µg/liter of iodine.

The arsenic reactant can be prepared as follows:

Analytically pure arsenic oxide (5.0 g) and analytically pure sodium chloride (8.09 g) are introduced into a 100 cc volumetric flask. A 10M sodium hydroxide solution (100 cc) is added, and the mixture is made up to 100 cc with twice-deionized water.

The iodine reference solution can be prepared as follows:

The arsenic reactant (5 cc) and a 1 mg/liter iodine reference solution (5 cc) are introduced into a 100 cc volumetric flask. The mixture is made up to 100 cc with deionized water.

The present invention also relates to a kit for determining the iodine content of drinking water.

The assay kit can consist of either:

a) two transparent colorless coaxial tubes described above a rigid and pointed tube graduated, such that it takes up a fixed amount of water to be analyzed or of iodine reference solution an ampoule or closed tube containing a stabilized aqueous iodine solution of known concentration. One tube is used for analyzing the water to be analyzed, the second one is used for carrying out a reference test with the iodine solution of known concentration, or:

b) 4 tubes containing the reactants described above and a sampling tube.

The comparison of the colorations obtained with the water to be analyzed and the reference solution makes it possible to determine whether the iodine concentration in the water to be analyzed is lower than, equal to or higher than the concentration of the reference solution.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. An apparatus for the determination of the presence of iodine in drinking water comprising:

a transparent outer tube which is closed at one end and contains a support containing a fixed amount of a cerium derivative, a transparent inner tube whose outer diameter corresponds to the inner diameter of the outer tube and which is partially engaged in the outer tube, which is closed at its end located in the inside of the outer tube by a pierceable film, which contains a support containing a fixed amount of an arsenic derivative and which is closed at its outer portion by a removable closure.

2. The apparatus according to claim 1, wherein the outer tube has a diameter about 1 cm and a tube wall thickness of about 1 mm.

3. The apparatus according to claim 1, wherein the outer and inner tubes are made of glass or of a transparent, rigid and colorless plastic material.

4. The apparatus according to claim 1, wherein the support containing the cerium derivative consists of silica uniformly impregnated with an acidified solution of pure cerium ammonium sulphate dihydrate.

5. The apparatus according to claim 1, wherein the support containing the arsenic derivative consists of silica impregnated with an arsenic oxide solution.

6. An assay kit for the determination of the iodine content of drinking water, which consists of:

the apparatus according to claim 1;

a rigid and pointed graduated tube; and an ampoule or tube containing a stabilized aqueous iodine solution of known concentration.

* * * * *